(12) United States Patent
Tariel et al.

(10) Patent No.: US 10,054,540 B2
(45) Date of Patent: Aug. 21, 2018

(54) DEVICE GENERATING EVANESCENT WAVES, AND METHOD FOR THE IMPLEMENTATION THEREOF

(71) Applicant: DIAFIR, Rennes (FR)

(72) Inventors: Hugues Tariel, Rennes (FR); Frédéric Charpentier, Rennes (FR)

(73) Assignee: DIAFIR, Rennes (FR)

( * ) Notice: Subject to any disclaimer, the term of this patent is extended or adjusted under 35 U.S.C. 154(b) by 0 days.

(21) Appl. No.: 15/114,631

(22) PCT Filed: Jan. 23, 2015

(86) PCT No.: PCT/FR2015/050168
§ 371 (c)(1),
(2) Date: Jul. 27, 2016

(87) PCT Pub. No.: WO2015/110767
PCT Pub. Date: Jul. 30, 2015

(65) Prior Publication Data
US 2016/0356705 A1    Dec. 8, 2016

(30) Foreign Application Priority Data

Jan. 27, 2014 (FR) ..................... 14 50661

(51) Int. Cl.
*G01N 21/35* (2014.01)
*G01N 21/3577* (2014.01)
(Continued)

(52) U.S. Cl.
CPC ....... *G01N 21/3577* (2013.01); *A61B 5/0075* (2013.01); *B01L 3/5088* (2013.01); *G01N 21/431* (2013.01); *G01N 21/49* (2013.01); *G01N 21/552* (2013.01); *G01N 33/487* (2013.01); *G02B 6/02395* (2013.01);
(Continued)

(58) Field of Classification Search
CPC .................................................. G01N 21/3577
See application file for complete search history.

(56) References Cited

U.S. PATENT DOCUMENTS

2008/0169430 A1* 7/2008 Kimura .............. G01N 21/6428
250/458.1
2011/0090484 A1* 4/2011 Osterlund ............ G01N 21/552
356/51
(Continued)

FOREIGN PATENT DOCUMENTS

FR       2 978 547 A1     2/2013
WO    2011/121086 A1    10/2011

OTHER PUBLICATIONS

Anne et al., "Fiber evanescent wave spectroscopy using the mid-infrared provides useful fingerprints for metabolic profiling in humans", Journal of Biomedical Optics, vol. 14, No. 5, Sep./Oct. 2009, pp. 054033-1 to 054033-9; in English.

(Continued)

*Primary Examiner* — David Porta
*Assistant Examiner* — Hugh H Maupin
(74) *Attorney, Agent, or Firm* — Westerman, Hattori, Daniels & Adrian, LLP

(57) ABSTRACT

The invention relates to a device (10) comprising a support (14) having a wave guide (42) allowing the propagation of light of at least one wavelength, generating evanescent waves outwards. According to the invention, the device comprises means for receiving a liquid sample, designed to receive the liquid sample upon contact of the wave guide (42) in such a way as to impregnate the wave guide with a portion of the liquid sample, and actuatable means for breaking the contact between the liquid sample and the wave guide (42).

23 Claims, 3 Drawing Sheets

(51) Int. Cl.
    *G01N 21/43*     (2006.01)
    *G01N 21/49*     (2006.01)
    *G01N 21/552*     (2014.01)
    *A61B 5/00*     (2006.01)
    *G01N 33/487*     (2006.01)
    *B01L 3/00*     (2006.01)
    *G02B 6/02*     (2006.01)
    *G01N 21/47*     (2006.01)

(52) U.S. Cl.
    CPC .. *A61B 2562/0233* (2013.01); *B01L 2200/026* (2013.01); *B01L 2200/027* (2013.01); *B01L 2300/0609* (2013.01); *B01L 2300/0654* (2013.01); *B01L 2400/065* (2013.01); *G01N 2021/4769* (2013.01); *G01N 2201/0846* (2013.01); *G01N 2201/0886* (2013.01)

(56) References Cited

U.S. PATENT DOCUMENTS

2011/0301047 A1     12/2011   Immink et al.
2013/0102066 A1     4/2013   Bureau et al.
2014/0233880 A1     8/2014   Tariel

OTHER PUBLICATIONS

Cui et al., "From Selenium—to Tellurium-Based Glass Optical Fibers for Infrared Spectroscopies", Molecules, vol. 18, No. 5, 2013, pp. 5373-5388; in English.

International Search Report and Written Opinion dated May 27, 2015 issued in corresponding application No. PCT/FR2015/050168; w/English partial translation and partial machine translation (18 pages).

\* cited by examiner

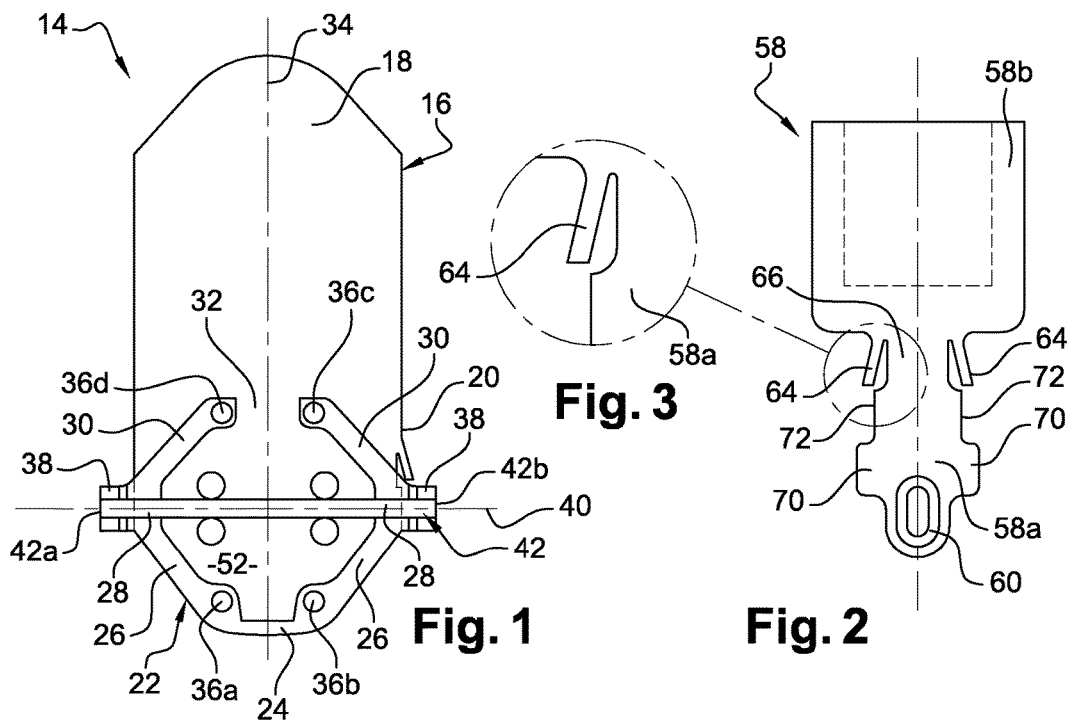
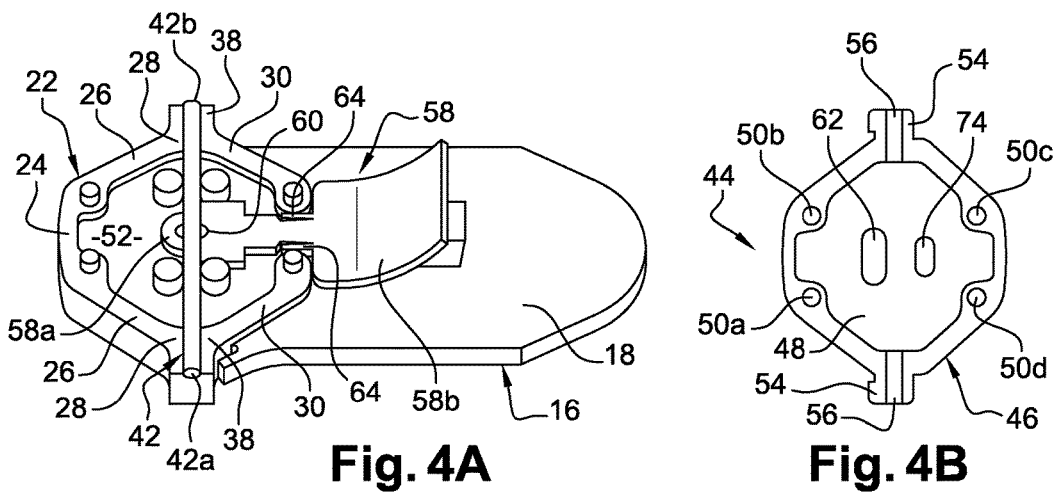
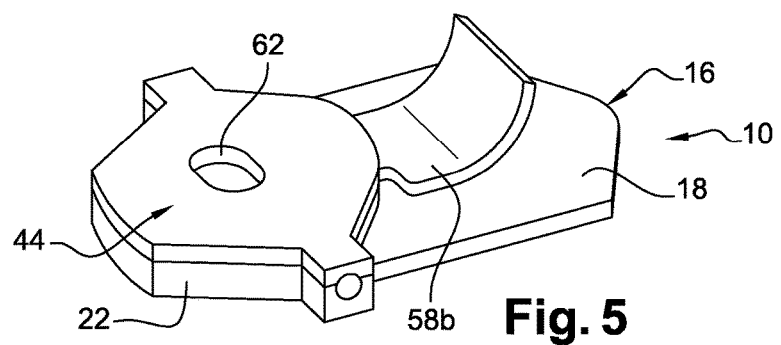

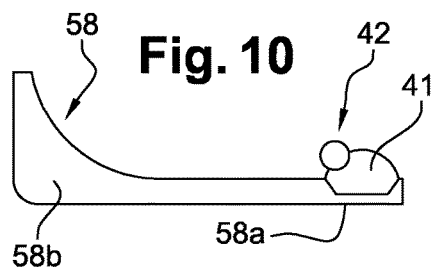
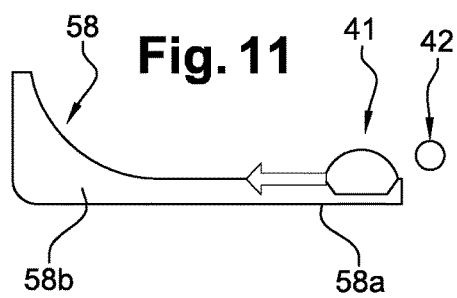
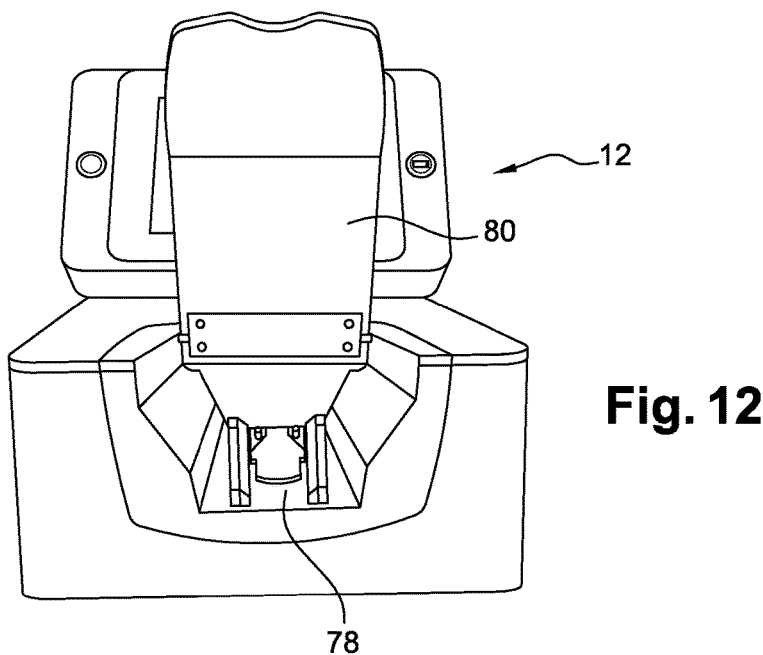
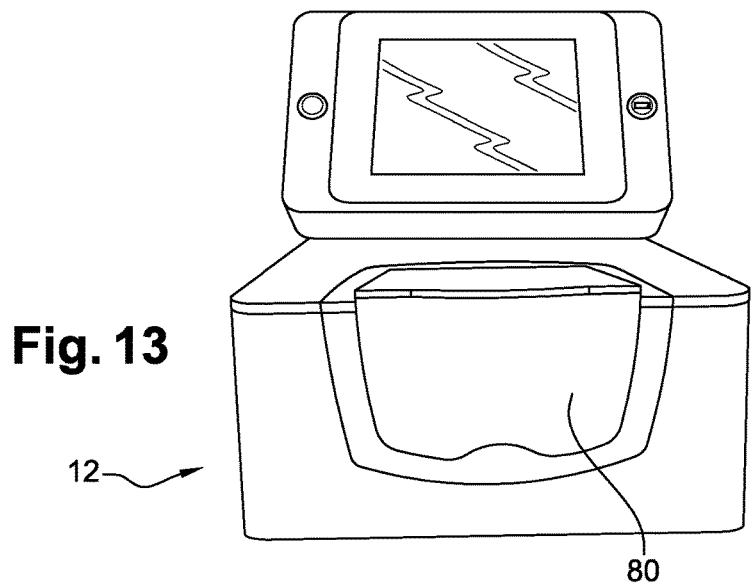

DEVICE GENERATING EVANESCENT WAVES, AND METHOD FOR THE IMPLEMENTATION THEREOF

The present invention relates to an evanescent wave absorption device and a spectrometry system comprising such a device and a method for implementing the device.

For over a decade, the scientific and medical community has been increasingly interested in the development of non-invasive diagnostic methods using optical fibers.

In particular, the evanescent wave sensors used for implementing an infrared spectrometric technique have especially well developed. The interest of this type of technique lies in using a fiber in which an evanescent wave travels through the outer surface of the fiber when infrared light propagates through the fiber.

When a biological sample is contacted with a wave guide, the evanescent wave interacts with the biological sample, which leads to the absorption of certain wavelengths of the evanescent infrared light.

The spectroscopic analysis then consists in comparing the spectrum obtained with and without a liquid sample in contact with the outer surface of the wave guide and deducing therefrom the substances present in the sample.

To carry out a spectroscopic analysis, the mid-infrared range, approximately ranging from 800-10,000 $cm^{-1}$, or the distant-infrared range, approximately ranging from 400 to 800 $cm^{-1}$, are usually used.

In particular, using an evanescent wave sensor in the form of an optical fiber which typically has a diameter of several hundred to several dozens of micrometers, with the diameter not necessarily being constant along the fiber, is known.

Document WO2011/121086 teaches to bend at least a portion of an optical fiber so as to create wave propagation distortions in the fiber, in order to locally increase the rate of evanescent waves at the curved portion and thereby increase the sensitivity of compounds detection in a biological sample.

However, for sensitivity reasons, evanescent waves optical fiber sensors generally use an optical fiber having a relatively small diameter. The curved portion is liable to break because of the material used and of the small diameter thereof.

Thus, adding means of protection against external mechanical damage to the curved portion of the fiber is known from document FR2978547 in the name of the Applicant.

As can be seen, improving the sensor sensitivity and reliability is thus crucial in the development of fiber sensors.

Eventually, in the case of a wave guide having a different shape from that of an optical fiber, it may be difficult or even impossible to change the curvature of the wave guide.

The invention particularly aims at improving the detection sensitivity, in a simple, effective and economical way.

For this purpose, it provides for a device comprising a support having a wave guide enabling the propagation of light in at least one wavelength generating evanescent waves outwards to detect optical signatures of an external medium in contact with the optical fiber, characterized in that it comprises means for receiving a liquid sample so configured as to receive the liquid sample upon contact with the wave guide so as to impregnate the wave guide with a portion of the liquid sample and actuatable means for breaking the contact between the liquid sample and the wave guide.

According to the invention, the device makes it possible to receive the liquid sample on the optical fiber and to deposit thereon the compounds or target molecules present in the sample and intended to be analyzed. Integrating actuatable contact breaking means makes it possible to subsequently remove the drop of liquid sample. The solvent present in the sample thus no longer impacts the measurement as is the case in the prior art.

If using an optical fiber with the curved portion as in the prior art is not necessary, it is of course possible.

According to another characteristic of the invention, said actuatable means comprise a member which is movable relative to the support and which comprises at least a portion of said receiving means, with the movable member being movable between a first position in which said receiving means are adapted to receive the liquid sample upon contact with the wave guide and a second position in which said receiving means are so configured that the liquid sample is no longer in contact with the wave guide.

The movable member is preferably so mounted as to be movable in translation on the support between the first and the second position thereof and in that the support comprises means for guiding the motion of the movable member between the first and the second position thereof.

Such guiding means may be pads projecting from the support and between which the movable member can move in translation.

The device preferably comprises means for locking the motion of the movable member from the second position to the first position when the movable member has been moved into the second position thereof.

Such means are desirable for preventing the movable member from returning to the first position thereof, which could lead to the sample coming again into contact with the optical fiber. This also ensures that each device will be used for the deposition of a single sample only and will be then disposed of upon completion of the analysis, thus preventing biological samples from being mixed up and misinterpretations of the results.

In practice, the operator places a drop of liquid in the receiving means provided for this purpose, moves the movable member from the first position to the second position thereof in which the movable member is prevented from returning to the first position thereof.

In a practical embodiment of the invention, said locking means comprise non-return pins or fingers formed on one of the support or the movable member and so configured as to be used as displacement stops on the other one of the support or the movable member upon the movable member moving from the second position to the first position thereof.

According to another characteristic of the invention, the device comprises a part forming a cover on the support and defining an enclosure accommodating a wave guide section with the support.

According to yet another characteristic of the invention, the wave guide can be attached to the support and the cover is sealed onto the support, for example by welding.

In a practical embodiment of the invention, the movable member is so mounted as to be movable in translation along a direction substantially perpendicular to the axis of propagation of light in the wave guide section, with the movable member comprising a portion accommodated inside the enclosure and which comprises a sump for receiving a liquid sample which is movable between the support and the wave guide section so that, in the first position of the movable member, the sump is arranged at right angles with the wave guide portion and in the second position, the sump is located at a distance from the wave guide section.

Advantageously, the cover comprises an aperture opening inside the enclosure opposite the receiving sump of the movable member when the latter is in the first position thereof.

It should be understood then that the operator injects the liquid using a pipette, for example, through the cover aperture so that the liquid is received in the receiving sump of the movable member when the latter is in the first position thereof.

The wave guide is preferably an optical fiber made of a material enabling the propagation of light in at least one infrared wavelength, such as chalcogenide glass fiber.

The invention further relates to a spectrometry system comprising a device of the type described above.

The invention also relates to a method for implementing the device described above and which comprises:

a) positioning a liquid sample in the receiving means;
b) letting the outer surface of the wave guide impregnate the liquid sample during a predetermined time;
c) actuating the contact breaking means so as to break the contact between the liquid sample and the optical fiber.

In a subsequent step of the method, the device obtained in step c) is positioned in a spectrometry system for spectroscopic analysis purposes.

The invention will be better understood and other details, advantages and characteristics of the invention will appear upon reading the following description given by way of non restrictive example, with reference to the accompanying drawings, wherein:

FIGS. 1 and 2 are schematic top views of the various parts forming the device according to the invention;

FIG. 3 is a schematic view on a larger scale of the enclosed area of FIG. 2;

FIG. 4A is a schematic perspective view of the device according to the invention without the cover;

FIG. 4B is a schematic perspective view of the cover of the device according to the invention;

FIG. 5 is a schematic perspective view of the device of the invention with the cover;

FIGS. 10 to 11 illustrate the principle of operation/use of the device according to the invention;

FIGS. 12 and 13 are schematic perspective views of a spectroscopy system comprising the device according to the invention.

Figure 6:
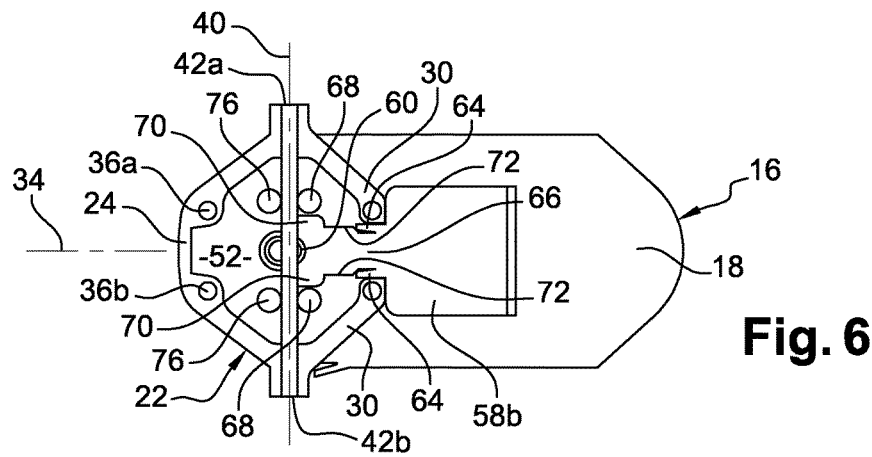
FIG. 6 is a schematic top view of the device according to the invention without the cover, with the movable member being in the first position thereof.

FIGS. 1 to 9 illustrate one embodiment of an optical fiber device 10 according to the invention and intended to be used with a spectroscopy system 12 as shown in FIGS. 12 and 13. The device comprises a support 14 comprising a support wall 16 having an elongate shape comprising a so-called gripping portion and an opposite portion 20 intended to form the optical fiber sensor itself. The gripping portion 18 may comprise parallel ridges (not shown) facilitating the holding of the device 10.

The optical fiber portion of the support comprises a rib 22 having a polygonal shape and extending substantially perpendicularly to the support wall 16. Such rib 22 comprises a first wall 24 formed at the end of the elongate support opposite the gripping portion 18 which extends at its ends into two second walls 26 away from each other which extend in two third walls 28 parallel to each other which are extended by two fourth walls 30 converging toward each other and defining, at the free ends thereof, a space 32 arranged opposite the first wall 24 along the elongated direction 34.

The ends of the first wall 24 and the free ends of the fourth walls 30 are provided with pads 36a, 36b, 36c, 36d protruding in a direction opposite the support wall.

The third walls 28 each carry a side lug 38, with the side lugs 38 extending in the same direction 40 perpendicular to the direction 34, but towards opposite aims and away from one another.

An optical fiber section 42 rests at its ends 42a, 42b on the side lugs 38 so as to extend in the direction 40.

As shown in FIG. 4B, the device 10 comprises a cover 44, the periphery of which carries a rim 46 extending perpendicularly to a bottom wall 48. The rim 46 forms a closed perimeter intended to bear on the rib 22 of the support 14. This rim 46 thus comprises four blind holes 50a, 50b, 50c, 50d formed thereon, so as to cooperate with the pads 36a, 36b, 36c, 36d of the first 24 and fourth 30 walls of the rib 22 of the support 14. The cover 44 thus placed on the rib 22 of the support 14 defines an enclosure 52 with the rib 22 and the support wall 16. The cover 44 also comprises two side lugs 54 suitable to be positioned on the lugs 38 of the support 14. Such side lugs 54 each comprise a notch 56 having a curved wall and the section of which is suitable for receiving the entire segment of the optical fiber section 42.

According to the invention, the device comprises means for receiving a drop in contact with the optical fiber and means actuatable to remove this drop after contact with the fiber section 42.

In the embodiment shown in the drawings, the actuatable means consist of a moving member 58 comprising a first part 58a arranged inside the enclosure and a second part 58b arranged outside the enclosure 52 and which can be gripped. The movable member 58 has an elongated shape along the direction 34 perpendicular to the axis 40 of the optical fiber section 42. The first portion 58a of the movable member 58 comprises a sump 60 at its end opposite the second part 58b. Such sump 60 is intended to receive the liquid sample as can be read in the description below. The height of the rib 22 of the support and the thickness of the first part 58a of the movable member 58 are so determined that the space between the portion of the optical fiber section within the enclosure 52 and the support wall is sufficient to introduce therein the first part 58a of the movable member 58.

Figure 7:
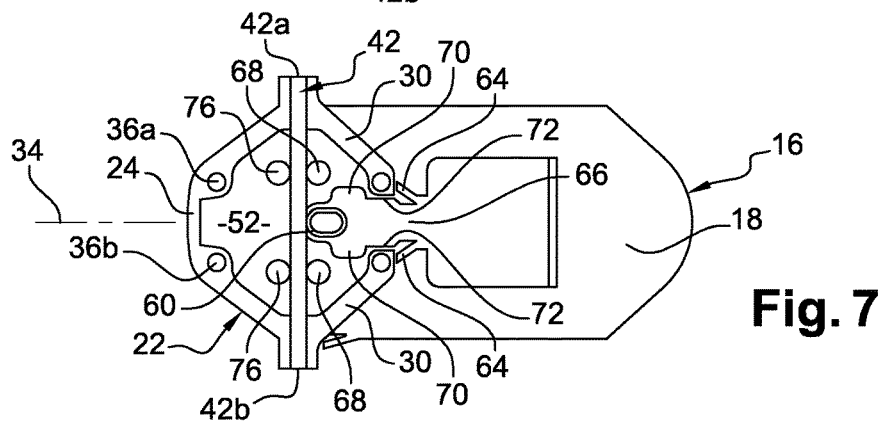
FIG. 7 is a schematic top view of the device according to the invention without the cover, with the movable member being in the second position thereof.

As shown in FIGS. 6 and 7, the movable member 58 is so mounted as to be translated on the support 14 between a first position (FIG. 6) in which the sump is inserted between the optical fiber 42 and the support wall 18 and a second position (FIG. 7) in which the sump 60 is placed away from the optical fiber section 42.

Figure 8:
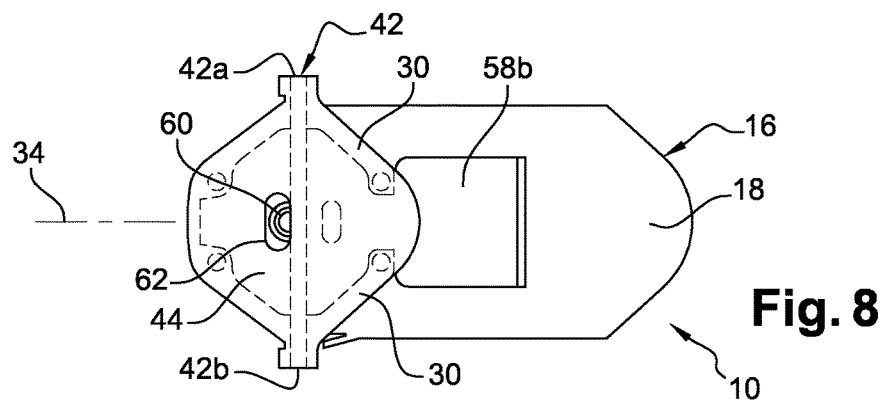
FIG. 8 is a schematic top view of the device according to the invention with the cover, with the movable member being in the first position thereof.
Figure 9:
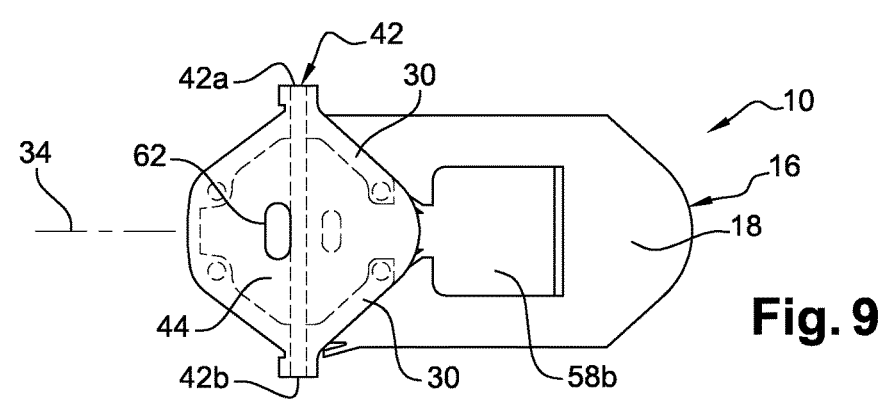
FIG. 9 is a schematic top view of the device according to the invention with the cover, with the movable member being in the second position thereof.

In order to make it possible to insert the drop of liquid sample into the sump 60, the cover 44 comprises an aperture 62 which is so arranged that, when the movable member 58 is in the first position thereof, the sump 60 is then aligned with the aperture (FIG. 8).

It should also be noted (FIG. 8) that the optical fiber 42 is not positioned opposite the aperture 62 in the cover 44 so as to prevent any damage which might be caused by the end of a pipette during the deposition of the liquid drop.

The movable member 58 comprises non-return means so arranged as to prevent the movable member 58 from returning to the first position thereof when it has been moved from the initial first position thereof to the second position thereof. For this purpose, it comprises non-return pins 64 or fingers extending on either side of a joint portion 66 joining the first part 58a of the movable member 58 and the second part 58b of the member (FIGS. 2, 4A, 6 and 7). Such pins are inclined relative to the axis 40 so as to diverge relative to each other in the direction opposite the displacement of the movable member 58.

In practice, when the movable member 58 is moved from the first position thereof to the second position thereof, the pins 64 initially pre-stressed along the middle portion 66 at the free ends of the fourth walls 30, laterally unfold as soon as the middle portion 66 is out of the enclosure 52, thus preventing a return of the movable member 58 to the first position thereof since the free ends of the pins 64 come to rest on the free ends of the fourth walls 30.

In order to facilitate the translational movement of the movable member 58, displacement guide means are provided. For this purpose, the inside of the enclosure 52 comprises two pads 68 between which lateral protrusions 70 of the first part 58a of the movable member 58 can come into contact. Similarly, such protrusions define two shoulders coming to rest onto the free ends of the fourth walls 30, when the movable member 58 is in the second position thereof, thereby preventing the disengagement of the movable member 58 from the support. The movable member 58 is thus permanently locked in the second position thereof.

The guide means also comprise two side surfaces 72 of the first part 58a which are substantially parallel and which are slidably supported by the free ends of the fourth walls 30 during the displacement of the movable member 58 from the first position thereof to the second position thereof.

The guide means further comprise a pad 74 formed on the bottom surface of the cover 44 and the size of which is so determined as to come into contact with the first part 58a and to prevent tilting of the movable member 58 during the displacement thereof which might damage the optical fiber 42.

The pads 68 and the other two additional pads 76 have identical heights so determined that they come into contact with the bottom of the cover 44 when the latter is mounted onto the rib 22 of the support.

The device according to the invention is positioned as follows: first the movable member 58 is arranged inside the enclosure 52 and the optical fiber section 42 is mounted on the lugs 38 of the rib 22 along the axis 40 and eventually the cover 44 is mounted on the rib 22 of the support 14 and welded thereon for example by fusion with the tip of a soldering iron. A drop of biological sample to be analyzed is inserted through the aperture 62 of the cover 44 to be received in the sump 60 of the movable member 58 which is then moved from the first position thereof (FIG. 10) to the second position thereof in which the liquid drop is no longer in contact with the optical fiber 42 (FIG. 11) and wherein the displacement of the movable member 58 on the support 14 is locked.

Eventually, during a last step, the optical fiber device is arranged in a recess 78 of a spectroscopy system 12 comprising means for connecting one of the ends 42b of the optical fiber section 42 to means emitting infrared light and the other end 42a to analyzing and processing means. The light emitted by the emitting means with the end 42a of the optical fiber and the light exiting the optical fiber can be coupled using lenses.

The system comprises a cover 80 intended to close and make the recess accommodating the optical fiber device opaque upon the emission of infrared light.

Without departing from the scope of the invention, the movable member could be a bottom wall of a sump which would be rotationally movable about an axis between a closed position in which it retains the biological fluid and an open position in which it allows the discharge of the biological fluid.

In practice, the means for receiving the biological sample are so configured as to receive a sample having a volume ranging from 5 to 20 µl.

Other types of guide means are also possible such as grooves and matching ribs formed on the movable member and the support wall.

The device may also comprise means for heating the optical fiber. Such means are advantageously actuated after removal of the sample liquid drop so as to remove liquid residues in contact with the optical fiber. It should be noted here that increasing the temperature to 35° C. makes it possible to shorten the measuring time by 50% by facilitating the discharge of the solvent, for example water.

According to an alternative device, the heating means can also be the means for removing the water drop, so that the movable means described above are no longer required.

According to still another alternative device, the means for removing the drop of water may include blowing means, for instance comprising air supply means at the contact area between the optical fiber and the drop of water. The device then also comprises means for removing the water drop.

The invention has been described while referring to the drawings in combination with an optical fiber. It should however be understood that it would be possible to use any type of wave guide enabling the propagation of waves and the generation of evanescent waves. Such wave guides can have, for instance, a strip shape as those used in the devices of the DNA biochip type, well known to the persons skilled in the art.

The invention claimed is:

1. A device adapted for coupling with a spectrometry system, the device comprising:
   a support having a wave guide attached to the support, the wave guide enabling the propagation of light in at least one wavelength, generating evanescent waves outwards,
   receiving means for receiving a liquid sample, configured to receive the liquid sample upon contact with the wave guide so as to impregnate the wave guide with a portion of the liquid sample, and
   actuatable means for breaking the contact between the liquid sample and the wave guide attached to the support, the actuatable means comprising a movable member which is movable relative to the support and which comprises at least a portion of the receiving means,
   wherein the movable member is movable between a first position in which the receiving means are adapted to receive the liquid sample upon contact with the wave guide and a second position in which the receiving means are configured so that the liquid sample is no longer in contact with the wave guide.

2. The device according to claim 1, wherein the movable member is mounted so as to be movable in translation on the support between the first and the second position thereof and wherein the support comprises means for guiding the motion of the movable member between the first and the second position thereof.

3. The device according to claim 2, which comprises means for locking the motion of the movable member from the second position to the first position when the movable member has been moved into the second position thereof.

4. The device according to claim 3, wherein the locking means comprise non-return pins or fingers formed on one of the support or the movable member, and configured to be used as displacement stops on the other one of the support or the movable member upon the movable member moving from the second position to the first position thereof.

5. The device according to claim 2, which comprises a part forming a cover on the support and defining an enclosure accommodating a wave guide section with the support.

6. The device according to claim 1, which comprises means for locking the motion of the movable member from the second position to the first position when the movable member has been moved into the second position thereof.

7. The device according to claim 6, wherein the locking means comprise non-return pins or fingers formed on one of the support or the movable member, and configured to be used as displacement stops on the other one of the support or the movable member upon the movable member moving from the second position to the first position thereof.

8. The device according to claim 6, which comprises a part forming a cover on the support and defining an enclosure accommodating a wave guide section with the support.

9. The device according to claim 7, which comprises a part forming a cover on the support and defining an enclosure accommodating a wave guide section with the support.

10. The device according to claim 1, which comprises a part forming a cover on the support and defining an enclosure accommodating a wave guide section with the support.

11. The device according to claim 10, wherein the movable member is mounted so as to be movable in translation along a direction substantially perpendicular to an axis of propagation of light in the wave guide section, the movable member comprising a portion accommodated inside the enclosure, wherein the portion comprises a sump for receiving a liquid sample, wherein the sump is movable between the support and the wave guide section so that, in the first position of the movable member, the sump is arranged at right angles with the wave guide section and in the second position, the sump is located at a distance from the wave guide section.

12. The device according to claim 11, wherein the cover comprises an aperture opening inside the enclosure opposite the receiving sump of the movable member when the movable member is in the first position thereof.

13. The device according to claim 1, wherein the cover is sealed on the support.

14. The device according to claim 13, wherein the cover is sealed on the support by welding.

15. The device according to claim 1, wherein the wave guide is heated.

16. The device according to claim 1, wherein the wave guide is made of a material enabling the propagation of light in at least one infrared wavelength.

17. The device according to claim 16, wherein the wave guide is made of chalcogenide glass fiber.

18. A spectrometric system, which comprises a device according to claim 1.

19. A method of implementing the device according to claim 1, comprising:
   a) positioning a liquid sample in the receiving means of the device;
   b) letting the outer surface of the wave guide impregnate with the liquid sample for a predetermined time; and
   c) actuating the contact breaking means so as to break the contact between the liquid sample and the optical fiber.

20. The method according to claim 19, comprising positioning the device obtained in c) in a spectrometric system.

21. The device according to claim 1, wherein the receiving means is a sump.

22. The device according to claim 1, wherein the wave guide is fixedly arranged relative to the support.

23. The device according to claim 1, wherein the wave guide has a surface adapted to be coupled to receive infrared light from the spectroscopy system and a second surface adapted to be coupled to send infrared light to the spectroscopy system for analysis.

* * * * *